United States Patent
Kaneko et al.

(10) Patent No.: US 6,645,442 B2
(45) Date of Patent: Nov. 11, 2003

(54) METHOD AND APPARATUS FOR PRODUCING METHANOL MAKING USE OF BIOMASS MATERIAL

(75) Inventors: Shozo Kaneko, Tokyo (JP); Yoshinori Kobayashi, Tokyo (JP); Tatsuo Kabata, Tokyo (JP); Takeshi Aruga, Tokyo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 0 days.

(21) Appl. No.: 10/001,809

(22) Filed: Dec. 5, 2001

(65) Prior Publication Data

US 2002/0087037 A1 Jul. 4, 2002

(30) Foreign Application Priority Data

Dec. 28, 2000 (JP) ........................................ 2000-400039

(51) Int. Cl.⁷ ............................... C10J 3/46; B09B 3/00
(52) U.S. Cl. ....................... 422/187; 422/188; 422/189; 422/190; 422/198; 204/275.1
(58) Field of Search ................................ 422/187–188, 422/198, 190, 199; 518/702, 704; 204/275.1; 48/61, 62 R

(56) References Cited

U.S. PATENT DOCUMENTS

| 4,993,348 | A | * | 2/1991 | Wald | .......................... | 114/265 |
| 5,310,506 | A | * | 5/1994 | Supp et al. | .................. | 252/373 |
| 5,344,848 | A | | 9/1994 | Steinberg et al. | ........... | 518/704 |

FOREIGN PATENT DOCUMENTS

| DE | 28 09 082 | | 11/1978 |
| EP | 0 066 498 | | 12/1982 |
| JP | 10-153165 A | * | 6/1998 |
| JP | 2948344 | | 7/1999 |
| JP | 2948345 | | 7/1999 |
| JP | 3009536 | | 12/1999 |
| JP | 3009541 | | 12/1999 |
| TW | 82100031 | | 1/1993 |

* cited by examiner

*Primary Examiner*—Hien Tran
(74) *Attorney, Agent, or Firm*—Oblon, Spivak, McClelland, Maier & Neustadt, P.C.

(57) ABSTRACT

The present invention provides a method for producing methanol making use of biomass material, which method is capable of making effective use of produced carbon monoxide without deteriorating efficiency of methanol production. The invention also provides an apparatus for producing methanol. In the method for producing methanol making use of biomass material including gasifying biomass to produce a gas and producing methanol from the produced gas, water is electrolyzed by means of a water electrolysis unit operated by electric power generated from a sunlight power-generation unit or a wind power-generation unit, and hydrogen gas generated through electrolysis of the water is supplied to the raw material gas such that the amount of hydrogen is adjusted to at least twice the amount of carbon monoxide contained in the produced gas, to thereby produce methanol in a methanol synthesis column.

3 Claims, 1 Drawing Sheet

METHOD AND APPARATUS FOR PRODUCING METHANOL MAKING USE OF BIOMASS MATERIAL

The entire disclosure of Japanese Patent Application No. 2000-400039 filed on Dec. 28, 2000, including specification, claims, drawing, and abstract is incorporated herein by reference in its entirety.

BACKGROUND OF THE INVENTION

1. Field of the Invention

The present invention relates to a method and apparatus for producing methanol making use of biomass as raw material.

2. Background Art

Production of methanol by use of biomass such as plants as a raw material is carried out on the basis of the following reactions.

$$CH_2O + \tfrac{1}{2}O_2 \rightarrow CO + H_2O \quad (1)$$

$$CO + H_2O \leftarrow\rightarrow H_2 + CO_2 \quad (2)$$

$$CO + 2H_2 \rightarrow CH_3OH \quad (3)$$

Briefly, carbon monoxide (CO) and hydrogen gas ($H_2$) which have been produced through partial combustion or steam-gasification of biomass ($CH_2O$) are caused to react, to thereby produce methanol ($CH_3OH$).

As used herein, the term "partial combustion" refers to a type of combustion in which a portion of biomass is subjected to combustion including complete and incomplete combustion.

As is clear from scheme (2), the aforementioned reactions include a shift reaction; i.e., when an attempt is made to increase the amount of carbon monoxide to be produced, the amount of hydrogen to be produced decreases, and when an attempt is made to increase the amount of hydrogen to be produced, the amount of carbon monoxide to be produced decreases. Generally, the reaction is shifted to the left side, where the amount of carbon monoxide to be produced increases. Therefore, the amount of hydrogen for producing methanol becomes insufficient, and the produced carbon monoxide cannot be used effectively.

One possible measure to solve this problem is to supply water (steam) to the reaction system, to thereby shift the reaction to the right side of the aforementioned scheme (2) so as to generate hydrogen of a required and sufficient amount. However, when the amount of supplied steam increases, the temperature in the reaction system is lowered, to thereby retard rate of reaction and problematically reduce efficiency of methanol production.

SUMMARY OF THE INVENTION

In view of the foregoing, the present inventors carried out extensive studies so as to solve the problems, and have found that methanol can be produced effectively by supplying hydrogen gas to a gas produced by gasifying biomass in a conventional method for producing methanol making use of biomass material. Thus, an object of the present invention is to provide a method for producing methanol making use of biomass material, which method is capable of making effective use of produced carbon monoxide without deteriorating efficiency of methanol production. Another object of the invention is to provide an apparatus for producing methanol.

Accordingly, in a first aspect of the present invention, there is provided a method for producing methanol making use of biomass material comprising gasifying biomass to produce a gas; and supplying hydrogen gas to the produced gas, to thereby produce methanol.

Preferably, hydrogen gas is supplied to the produced gas such that the amount of hydrogen gas is adjusted to at least twice the amount of carbon monoxide contained in the produced gas.

Preferably, hydrogen gas generated through electrolysis of water is supplied to the produced gas.

Preferably, oxygen gas generated through electrolysis of water is employed as a gasification agent for the biomass.

Preferably, hydrogen gas and oxygen gas generated through electrolysis of water are temporarily reserved separately before use.

Preferably, water is electrolyzed by electric power obtained by use of natural energy (i.e., energy obtained from natural resources).

Preferably, the electric power obtained by use of natural energy is temporarily stored before use.

Preferably, the natural energy is at least one type of energy selected from among sunlight energy, wind energy, tidal energy, hydraulic energy, and solar thermal energy.

In a second aspect of the present invention, there is provided an apparatus for producing methanol making use of biomass material comprising biomass gasification means for producing a gas through partial combustion or steam-gasification of biomass; methanol synthesis means for producing methanol from the thus-produced gas; and hydrogen gas supplying means for supplying hydrogen gas to the produced gas.

Preferably, the hydrogen gas supplying means supplies hydrogen gas to the produced gas such that the amount of hydrogen gas is adjusted to at least twice the amount of carbon monoxide contained in the produced gas.

Preferably, the hydrogen gas supplying means includes water electrolysis means for electrolyzing water.

Preferably, oxygen gas generated through electrolysis of water by means of the water electrolysis means is supplied, as a gasification agent, to the biomass gasification means.

Preferably, the above apparatus for producing methanol further comprises oxygen gas reserving means for temporarily reserving oxygen gas generated through electrolysis of water by means of the water electrolysis means, and the hydrogen gas supplying means includes hydrogen gas reserving means for temporarily reserving hydrogen gas generated through electrolysis of water by means of the water electrolysis means.

Preferably, the above apparatus for producing methanol further comprises natural-energy-based power-generation means for operating the water electrolysis means through power generation making use of natural energy.

Preferably, the natural-energy-based power-generation means includes electric power storage means for temporarily storing electric power.

Preferably, the natural-energy-based power-generation means generates electric power by use of at least one type of energy selected from among sunlight energy, wind energy, tidal energy, hydraulic energy, and solar thermal energy.

BRIEF DESCRIPTION OF THE DRAWING

Various other objects, features, and many of the attendant advantages of the present invention will be readily appreciated as the same becomes better understood with reference to the following detailed description of the preferred embodiments when considered in connection with an accompanying drawing, in which.

DETAILED DESCRIPTION OF PREFERRED EMBODIMENTS

Figure 1:
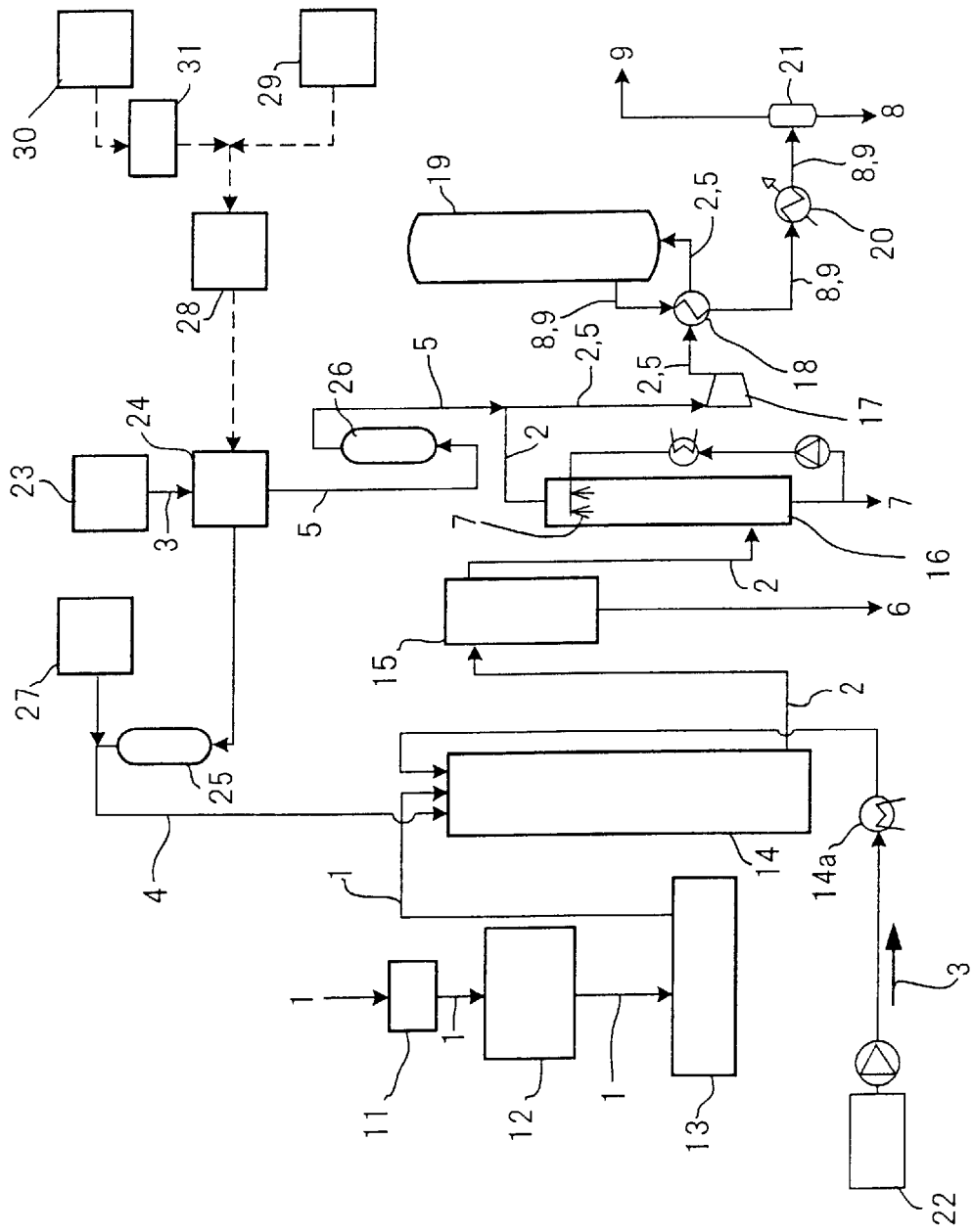
FIG. 1 shows a schematic diagram in relation to one embodiment of the apparatus for producing methanol making use of biomass material according to the present invention.

Embodiments of the method and apparatus for producing methanol making use of biomass material according to the present invention will be described with reference to FIG. 1. FIG. 1 shows a schematic diagram in relation to the apparatus for producing methanol.

As shown in FIG. 1, a dryer 11 for drying biomass 1 such as trees and other plants is connected to the inlet of a hopper 12. The outlet of the hopper 12 is connected to the inlet of a pulverizer 13 for pulverizing dried biomass 1.

The outlet of the pulverizer 13 is connected to the inlet of a gasification furnace 14 serving as biomass gasification means for causing produced gas 2 to be produced through partial combustion or steam-gasification of biomass 1. The outlet of the gasification furnace 14 is connected to the inlet of a dust collecting unit 15 for removing ash 6 from the produced gas 2. The gas outlet of the dust collecting unit 15 is connected to the gas inlet of a scrubber 16 for washing and cooling the produced gas 2 by spraying washing water 7.

The gas outlet of the scrubber 16 is connected, via a pressure-elevating apparatus 17 and a heat exchanger 18, to the inlet of a methanol synthesis column 19 serving as methanol synthesis means for producing methanol 8 from the produced gas 2. The outlet of the methanol synthesis column 19 is connected, via the heat exchanger 18 and a heat exchanger 20, to a reservoir 21 for reserving methanol 8.

To the gasification furnace 14, a water supplier 22 is connected via a heat exchanger 14a. When water 3 is supplied from the water supplier 22, the heat exchanger 14a vaporizes water 3 by heating, and the thus-produced steam is supplied into the gasification furnace 14.

To the gasification furnace 14 is also connected an oxygen gas outlet of a water electrolysis unit 24 for electrolyzing water 3 to form oxygen gas 4 and hydrogen gas 5. Between the gasification furnace 14 and the oxygen gas outlet of the water electrolysis unit 24, an oxygen gas tank 25 serving as oxygen gas reserving means for temporarily reserving oxygen gas 4 is provided. The hydrogen gas outlet of the water electrolysis unit 24 is connected to a position between the pressure-elevating apparatus 17 and the gas-outlet of the scrubber 16. A hydrogen gas tank 26 serving as hydrogen gas reserving means for temporarily reserving hydrogen gas 5 is inserted between the pressure-elevating apparatus 17 and the hydrogen gas outlet of the water electrolysis unit 24.

To the water electrolysis unit 24, a water supplier 23 for supplying water 3 is connected. An auxiliary oxygen gas source 27 for supplementing oxygen gas 4 is inserted between the oxygen gas tank 25 and the gasification furnace 14.

The water electrolysis unit 24 is connected to a secondary cell 28 serving as electric power storage means for temporarily storing electric power. The secondary cell 28 is connected to a sunlight power-generation unit 29 serving as natural-energy-based power-generation means for generating power by use of sunlight energy, and is connected, via an AC/DC converter 31, to a wind power-generation unit 30 serving as natural-energy-based power-generation means for generating power by use of wind energy.

In this embodiment, the water electrolysis means comprises the water supplier 23, the water electrolysis unit 24, etc., and the hydrogen gas supplying means comprises the water electrolysis means, the hydrogen gas tank 26, etc.

The method for producing methanol employing such an apparatus for producing methanol will next be described.

Electric power is generated by means of the sunlight power-generation unit 29 and the wind power-generation unit 30, and the thus-generated electric power is temporarily stored in the secondary cell 28. The water electrolysis unit 24 is operated by utilizing the stored electric power, to thereby electrolyze water 3 supplied from the water supplier 23. The thus-produced oxygen gas 4 is temporarily reserved in the oxygen gas tank 25, and the thus-produced hydrogen gas 5 is temporarily reserved in the hydrogen gas tank 26.

Subsequently, the biomass 1 is dried in the dryer 11, fed into the hopper 12, and supplied from the hopper 12 into the pulverizer 13, where the biomass 1 is pulverized. The pulverized biomass is supplied into the gasification furnace 14. Oxygen gas 4 is supplied from the oxygen gas tank 25 into the gasification furnace 14, to thereby cause partial combustion. Furthermore, water 3 is supplied from the water supplier 22 to the heat exchanger 14a for heating, to thereby generate high-temperature steam (400–500° C.). The steam is supplied into the gasification furnace 14. Thus, the biomass ($CH_2O$) 1 is decomposed, to thereby generate the produced gas (CO, $H_2$) 2 based on the following schemes.

  (1)

  (2)

As is clear from the aforementioned scheme (2), the produced gas 2 undergoes a shift reaction; i.e., when an attempt is made to increase the amount of carbon monoxide to be produced, the amount of hydrogen gas to be produced decreases, and when an attempt is made to increase the amount of hydrogen gas to be produced, the amount of carbon monoxide to be produced decreases. Generally, the reaction is shifted to the left side, where the amount of carbon monoxide to be produced increases. Therefore, the amount of hydrogen for producing methanol remains insufficient.

The produced gas 2 generated in the aforementioned gasification furnace 14 is supplied into the dust collecting unit 15, to thereby remove ash 6 and like matter. Subsequently, the gas is supplied into the scrubber 16, and cooled and washed by being sprayed with washing water 7. Then, the gas is transferred from the scrubber 16.

Hydrogen gas 5 supplied from the aforementioned hydrogen gas tank 26 is added to the produced gas 2, such that the amount of hydrogen is adjusted to at least twice the amount of carbon monoxide. The amount of added hydrogen can be set by analyzing in advance the composition of the biomass 1 and taking into consideration conditions such as gasification conditions in the gasification furnace 14. There may also be provided a control system for measuring the carbon monoxide content and the hydrogen content of the produced gas 2 fed from the scrubber 16 by means of a sensor or like apparatus and for supplying, based on the measurement, hydrogen gas 5 from the hydrogen gas tank 26 such that the amount of hydrogen becomes at least twice the amount of carbon monoxide contained in the produced gas 2.

The pressure of the thus-treated produced gas 2 containing hydrogen in an amount at least twice the amount of carbon monoxide is elevated by means of the pressure-elevating apparatus 17, and supplied, via the heat exchanger 18, into the methanol synthesis column 19, to thereby produce the methanol ($CH_3OH$) 8 based on the following scheme.

$$CO + 2H_2 \rightarrow CH_3OH \quad (3)$$

The aforementioned methanol 8 is supplied, via the heat exchangers 18 and 20, into the reservoir 21 for reservation, and discharge gas 9 is discharged to the outside of the system.

Briefly, hydrogen gas 5 deficient in amount with respect to carbon monoxide contained in the produced gas 2 formed from the biomass 1 is supplemented, and then methanol 8 is produced.

Therefore, methanol 8 can be produced by fully consuming carbon monoxide contained in the produced gas 2 without leaving carbon monoxide.

Thus, according to the method for producing methanol and apparatus, the biomass 1 can be utilized effectively, leading to effective utilization of resources. In addition, the efficiency of forming methanol 8 can be remarkably enhanced, to thereby reduce production costs.

Since oxygen gas 4 formed through electrolysis of water 3 so as to obtain hydrogen gas 5 is employed for partial combustion in the gasification furnace 14, water 3 can be utilized effectively, leading to effective utilization of resources and a reduction in production costs.

In addition, since electric power generated by means of the sunlight power-generation unit 29 and the wind power-generation unit 30; i.e., natural energy, is utilized for electrolyzing water 3, effective utilization of energy can be attained, to thereby reduce production costs.

In addition, since the electric power generated by use of natural energy is temporarily stored in the secondary cell 28, electrolysis of water 3 by means of the water electrolysis unit 24 can be performed steadily and reliably.

Since oxygen gas 4 and hydrogen gas 5 which have been obtained through electrolysis of water 3 are temporarily reserved in the tanks 25 and 26, respectively, before use, each of these gases 4 and 5 can be readily utilized in a required amount while electrolysis of water 3 by means of the water electrolysis unit 24 is performed under predetermined conditions.

Examples of the biomass 1 which is used in the present invention include biological resources (e.g., agricultural products or by-products; lumber; plants; etc.) that can be utilized as an energy source or industrial raw material. Examples of such biological resources include sweet sorghum, nepiergrass, and spirulina, as well as agricultural and forest-originating wastes such as rice bran, wood chips, and lumber produced in thinning. In order to avoid complexity, the biomass 1 has been described by use of the composition represented by $CH_2O$. However, the composition of the biomass 1 is generally represented by $(C_xH_2O_y)_n$ (x=1.1–1.2; y=0.8–0.9; n is an integer.

The average particle size of the biomass 1 to be supplied into the gasification furnace 14 is preferably 0.05–5 mm. The reason is as follows. When the size is less than 0.05 mm, pulverization efficiency of the pulverizer 13 becomes poor, whereas when the size is in excess of 5 mm, partial combustion for decomposition that reaches the core portion of the biomass is difficult to attain, to thereby deteriorate the gasification efficiency.

The temperature of gasifying the biomass 1 in the gasification furnace 14 is preferably 700–1400° C., more preferably 800–1000° C. The reason is as follows. When the temperature is lower than 700° C., favorable partial combustion is difficult to attain, whereas when the temperature is in excess of 1400° C., the biomass 1 itself is combusted, to thereby unfavorably increase the percent generation of hydrocarbons such as soot.

No particular limitation is imposed on the pressure for gasifying the biomass 1 in the gasification furnace 14.

Although a gasification pressure of approximately 80 atm enables the gasification furnace 14 to be connected with the methanol synthesis column 19 without inserting the pressure-elevating apparatus 17 therebetween, the gasification furnace 14 is required to have high resistance to pressure, thereby elevating the cost of the gasification furnace 14. Thus, a gasification pressure of 1–40 atm is preferred, in that the pressure resistance required for the gasification furnace 14 can be reduced to a generally acceptable level. Particularly, a gasification pressure of 1–30 atm is remarkably preferred in that the dimensions of the gasification furnace 14 can be made relatively small.

Although the superficial velocity in the gasification furnace 14 is not particularly limited, a superficial velocity of 0.1–5 m/s is preferred. The reason is as follows. When the superficial velocity is less than 0.1 m/s, the residence time of the biomass 1 in the furnace is excessively prolonged, promoting conversion of the biomass 1 to hydrocarbon, whereas when the superficial velocity is in excess of 5 m/s, the residence time of the biomass 1 in the furnace is excessively shortened, making decomposition of biomass 1 through sufficient partial combustion difficult.

Particularly, when the average particle size of the biomass 1 is 0.05–1 mm, the superficial velocity in the gasification furnace 14 is controlled to 0.4–1 m/s, and when the average particle size is 1–5 mm, the superficial velocity in the gasification furnace 14 is controlled to 1–5 m/s. These conditions are particularly preferred, since the biomass 1 can be transferred under optimum conditions.

In this embodiment, the sunlight power-generation unit 29 utilizing sunlight energy and the wind power-generation unit 30 utilizing wind energy are employed in combination as natural-energy-based power-generation means utilizing natural energy. In accordance with the performance of power generation, either of the two power-generation units may be used singly, or may be used in combination with another power-generation unit such as tidal power-generation unit utilizing tidal energy, hydraulic power-generation unit utilizing hydraulic energy, or solar thermal power-generation unit utilizing solar thermal energy, so as to obtain electric power.

In this embodiment, water 3 to be supplied to the gasification furnace 14 is fed from the water supplier 22, and water 3 to be supplied to the water electrolysis unit 24 is fed from the water supplier 23. However, water 3 to be supplied to the gasification furnace 14 and that to be supplied to the water electrolysis unit 24 may also be fed from the same water supplier.

According to the method for producing methanol making use of biomass material of the present invention comprising gasifying biomass to produce a gas and producing methanol from the produced gas, hydrogen gas is supplied to the produced gas, to thereby produce methanol. Therefore, methanol can be produced by fully consuming carbon monoxide contained in the produced gas without leaving carbon monoxide. Thus, biomass can be utilized effectively, leading to effective utilization of resources. In addition, the efficiency of forming methanol can be remarkably enhanced, to thereby reduce production costs.

According to the apparatus for producing methanol making use of biomass material of the present invention comprising biomass gasification means for producing a gas through partial combustion or steam-gasification of biomass, and methanol synthesis means for producing methanol from the produced gas, the apparatus further comprises hydrogen gas supplying means for supplying hydrogen gas to the produced gas. Therefore, methanol can be produced by fully consuming carbon monoxide contained in the produced gas without leaving carbon monoxide. Thus, biomass can be utilized effectively, leading to effective utilization of resources. In addition, the efficiency of forming methanol can be remarkably enhanced, to thereby reduce production costs.

What is claimed is:

1. An apparatus for producing methanol making use of biomass material comprising:

biomass gasification means for producing a gas through partial combustion or steam-gasification of biomass;

methanol synthesis means for producing methanol from the thus-produced gas, hydrogen gas supplying means for supplying hydrogen gas to the produced gas, wherein the hydrogen gas supplying means supplies hydrogen gas to the produced gas such that the amount of hydrogen gas is adjusted to at least twice the amount of carbon monoxide contained in the produced gas and wherein the hydrogen gas supplying means includes water electrolysis means for electrolyzing water wherein oxygen gas generated through electrolysis of water by means of the water electrolysis means is supplied, as a gasification agent, to the biomass gasification means;

oxygen gas reserving means for temporarily reserving oxygen gas generated through electrolysis of water by means of the water electrolysis means, wherein the hydrogen gas supplying means includes hydrogen gas reserving means for temporarily reserving hydrogen gas generated through electrolysis of water by means of the water electrolysis means; and natural-energy-based power-generation means for operating the water electrolysis means through power generation making use of natural energy.

2. An apparatus for producing methanol making use of biomass material according to claim 1, wherein the natural-energy-based power-generation means includes electric power storage means for temporarily storing electric power.

3. An apparatus for producing methanol making use of biomass material according to claim 1, wherein the natural-energy-based power generation means generates electric power by use of at least one type of energy selected from among sunlight energy, wind energy, tidal energy, hydraulic energy, and solar thermal energy.

* * * * *